(12) United States Patent
Anand et al.

(10) Patent No.: US 11,783,134 B2
(45) Date of Patent: *Oct. 10, 2023

(54) GAP IN CARE DETERMINATION USING A GENERIC REPOSITORY FOR HEALTHCARE

(71) Applicant: CERNER INNOVATION, INC., Kansas City, KS (US)

(72) Inventors: Vikram Anand, Downingtown, PA (US); Farbod Rahmanian, Leesport, PA (US); William Michael Hasling, Princeton Junction, NJ (US); Brian Thornton, Collegeville, PA (US); Muthu Premananth, Banaglore (IN); Daniel Antohe, Englewood, CO (US); Radu Stefan Niculescu, Malvern, PA (US); Camille Anne Egan, Downingtown, PA (US); Bette Jane Reese, Chadds Ford, PA (US); William A. Landi, Devon, PA (US); Todd W. Fritsche, Phoenixville, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/574,384

(22) Filed: Jan. 12, 2022

(65) Prior Publication Data

US 2022/0138436 A1 May 5, 2022

Related U.S. Application Data

(63) Continuation of application No. 16/704,958, filed on Dec. 5, 2019, now Pat. No. 11,256,876, which is a
(Continued)

(51) Int. Cl.
*G06F 40/40* (2020.01)
*G16H 50/20* (2018.01)
*G16H 50/70* (2018.01)

(52) U.S. Cl.
CPC ............. *G06F 40/40* (2020.01); *G16H 50/20* (2018.01); *G16H 50/70* (2018.01)

(58) Field of Classification Search
CPC ......... G06F 17/28; G06F 19/00; G16H 50/20; G16H 50/70
See application file for complete search history.

(56) References Cited

U.S. PATENT DOCUMENTS

| 5,692,125 A | 11/1997 | Schloss et al. |
| 5,738,102 A | 4/1998 | Lemelson |

(Continued)

FOREIGN PATENT DOCUMENTS

| EP | 0854431 A2 | 7/1998 |
| EP | 0950971 A2 | 10/1999 |

(Continued)

OTHER PUBLICATIONS

Reich, Christian; Ryan, Patrick B; Stang, Paul E; Rocca, Mitra. Evaluation of alternative standardized terminologies for medical conditions within a network of observational healthcare databases. Journal of Biomedical Informatics45.4: 689-696. Academic Press Inc Elsevier Science. (Aug. 2012)) (Year: 2012).*

(Continued)

*Primary Examiner* — Linh Giang Le
(74) *Attorney, Agent, or Firm* — Kilpatrick Townsend & Stockton LLP

(57) ABSTRACT

By extracting clinical data of any format from respective different sources, a data repository normalized to a generic format is created. A medical domain specific language may be used to interact with the data repository for identifying
(Continued)

cohorts and gaps in care for the respective cohorts. Any rules for finding gaps in care are converted into the medical domain specific language for determining gaps. This standardization in both the data repository and rule application may allow for a true cost and time to value solution accessible to many different medical practices.

20 Claims, 4 Drawing Sheets

Related U.S. Application Data continuation of application No. 14/331,320, filed on Jul. 15, 2014, now Pat. No. 10,540,448, which is a continuation-in-part of application No. 14/037,469, filed on Sep. 26, 2013, now abandoned.

(60) Provisional application No. 61/846,111, filed on Jul. 15, 2013.

(56) References Cited

U.S. PATENT DOCUMENTS

| | | | |
|---|---|---|---|
| 5,786,816 A | 7/1998 | Macrae et al. | |
| 5,826,239 A | 10/1998 | Du et al. | |
| 5,832,448 A | 11/1998 | Brown | |
| 5,918,226 A | 6/1999 | Tarumi et al. | |
| 5,935,060 A | 8/1999 | Iliff | |
| 6,004,276 A | 12/1999 | Wright et al. | |
| 6,037,940 A | 3/2000 | Schroeder et al. | |
| 6,073,109 A | 6/2000 | Flores et al. | |
| 6,081,786 A | 6/2000 | Barry et al. | |
| 6,139,494 A | 10/2000 | Cairnes | |
| 6,151,583 A | 11/2000 | Ohmura et al. | |
| 6,208,974 B1 | 3/2001 | Campbell et al. | |
| 6,212,526 B1 | 4/2001 | Chaudhuri et al. | |
| 6,277,071 B1 | 8/2001 | Hennessy et al. | |
| 6,278,977 B1 | 8/2001 | Agrawal et al. | |
| 6,279,042 B1 | 8/2001 | Ouchi | |
| 6,282,531 B1 | 8/2001 | Haughton et al. | |
| 6,338,039 B1 | 1/2002 | Lonski et al. | |
| 6,345,260 B1 | 2/2002 | Cummings et al. | |
| 6,354,299 B1 | 3/2002 | Fischell et al. | |
| 6,401,138 B1 | 6/2002 | Judge et al. | |
| 6,421,649 B1 | 7/2002 | Rattner | |
| 6,458,080 B1 | 10/2002 | Brown et al. | |
| 6,468,210 B2 | 10/2002 | Iliff | |
| 6,523,019 B1 | 2/2003 | Borthwick | |
| 6,551,243 B2 | 4/2003 | Bocionek et al. | |
| 6,551,266 B1 | 4/2003 | Davis, Jr. | |
| 6,587,829 B1 | 7/2003 | Camarda et al. | |
| 6,641,532 B2 | 11/2003 | Iliff | |
| 6,714,913 B2 | 3/2004 | Brandt et al. | |
| 6,801,227 B2 | 10/2004 | Bocionek et al. | |
| 6,903,194 B1 | 6/2005 | Sato et al. | |
| 6,915,265 B1 | 7/2005 | Johnson | |
| 7,130,457 B2 | 10/2006 | Kaufman et al. | |
| 7,310,607 B2 | 12/2007 | Brandt et al. | |
| 7,438,216 B2 | 10/2008 | Ambekar et al. | |
| 7,447,644 B2 | 11/2008 | Brandt et al. | |
| 7,451,096 B2 | 11/2008 | Rucker | |
| 7,546,245 B2 | 6/2009 | Surpin et al. | |
| 7,617,078 B2 | 11/2009 | Rao et al. | |
| 7,653,558 B2 | 1/2010 | Schoenberg | |
| 7,653,873 B2 | 1/2010 | Brandt et al. | |
| 7,689,441 B1 | 3/2010 | Craft | |
| 7,693,730 B2 | 4/2010 | Hasan et al. | |
| 7,765,114 B2 | 7/2010 | Frick | |
| 7,810,045 B2 | 10/2010 | Weber | |
| 7,895,055 B2 | 2/2011 | Schneider et al. | |
| 7,908,153 B2 | 3/2011 | Scherpbier et al. | |
| 8,073,710 B2 | 12/2011 | Hasan et al. | |
| 8,290,786 B2 | 10/2012 | Ika et al. | |
| 8,364,499 B2 | 1/2013 | Maughan et al. | |
| 8,392,232 B2 | 3/2013 | Mcgillin | |
| 8,554,480 B2 | 10/2013 | Grigsby et al. | |
| 10,540,448 B2 | 1/2020 | Anand et al. | |
| 2002/0095313 A1 | 7/2002 | Haq | |
| 2002/0120187 A1 | 8/2002 | Eiffert et al. | |
| 2002/0120471 A1 | 8/2002 | Drazen | |
| 2003/0036683 A1 | 2/2003 | Kehr et al. | |
| 2003/0036923 A1 | 2/2003 | Waldon et al. | |
| 2003/0046114 A1 | 3/2003 | Davies et al. | |
| 2003/0050797 A1 | 3/2003 | Brandt et al. | |
| 2003/0050821 A1 | 3/2003 | Brandt et al. | |
| 2003/0055679 A1 | 3/2003 | Soll et al. | |
| 2003/0120133 A1 | 6/2003 | Rao et al. | |
| 2003/0120134 A1 | 6/2003 | Rao et al. | |
| 2003/0120458 A1 | 6/2003 | Rao et al. | |
| 2003/0120514 A1 | 6/2003 | Rao et al. | |
| 2003/0125984 A1 | 7/2003 | Rao et al. | |
| 2003/0125985 A1 | 7/2003 | Rao et al. | |
| 2003/0125988 A1 | 7/2003 | Rao et al. | |
| 2003/0126101 A1 | 7/2003 | Rao et al. | |
| 2003/0130871 A1 | 7/2003 | Rao et al. | |
| 2003/0171659 A1 | 9/2003 | Dean | |
| 2003/0212580 A1 | 11/2003 | Shen | |
| 2004/0002873 A1 | 1/2004 | Sachdeva | |
| 2004/0024616 A1 | 2/2004 | Spector et al. | |
| 2004/0078231 A1 | 4/2004 | Wilkes et al. | |
| 2004/0078236 A1 | 4/2004 | Stoodley et al. | |
| 2004/0172297 A1 | 9/2004 | Rao et al. | |
| 2005/0131738 A1 | 6/2005 | Morris | |
| 2005/0144187 A1 | 6/2005 | Che et al. | |
| 2005/0182659 A1 | 8/2005 | Huttin | |
| 2005/0187797 A1 | 8/2005 | Johnson | |
| 2005/0261941 A1 | 11/2005 | Scarlat | |
| 2006/0122865 A1 | 6/2006 | Preiss et al. | |
| 2007/0055552 A1 | 3/2007 | St et al. | |
| 2007/0185739 A1 | 8/2007 | Ober et al. | |
| 2008/0097792 A1 | 4/2008 | Marge | |
| 2008/0201280 A1 | 8/2008 | Martin et al. | |
| 2008/0255880 A1 | 10/2008 | Beller et al. | |
| 2008/0275731 A1 | 11/2008 | Rao et al. | |
| 2009/0018882 A1 | 1/2009 | Burton et al. | |
| 2009/0076845 A1 | 3/2009 | Bellin et al. | |
| 2009/0089097 A1 | 4/2009 | Schoenberg | |
| 2009/0138279 A1 | 5/2009 | Avinash et al. | |
| 2009/0204439 A1 | 8/2009 | Turton | |
| 2009/0210252 A1 | 8/2009 | Silver | |
| 2010/0094659 A1 | 4/2010 | Schoenberg | |
| 2011/0077972 A1 | 3/2011 | Breitenstein et al. | |
| 2011/0077973 A1 | 3/2011 | Breitenstein et al. | |
| 2011/0131060 A1 | 6/2011 | Schuster et al. | |
| 2011/0295616 A1 | 12/2011 | Vesto | |
| 2011/0295622 A1 | 12/2011 | Farooq et al. | |
| 2011/0301976 A1 | 12/2011 | Davis et al. | |
| 2011/0301982 A1* | 12/2011 | Green, Jr. | G16H 40/67 705/3 |
| 2012/0065987 A1 | 3/2012 | Farooq et al. | |
| 2012/0109689 A1 | 5/2012 | Lee | |
| 2012/0166220 A1 | 6/2012 | Baldwin et al. | |
| 2012/0166226 A1 | 6/2012 | Lee et al. | |
| 2012/0173277 A1 | 7/2012 | Yates et al. | |
| 2012/0215560 A1 | 8/2012 | Ofek et al. | |
| 2012/0231959 A1 | 9/2012 | Elton et al. | |
| 2013/0024211 A1 | 1/2013 | Monteforte et al. | |
| 2013/0085780 A1 | 4/2013 | Braunstein et al. | |
| 2013/0173295 A1 | 7/2013 | Hyde et al. | |
| 2014/0095203 A1 | 4/2014 | Anand et al. | |
| 2014/0095204 A1 | 4/2014 | Fung et al. | |
| 2015/0019248 A1 | 1/2015 | Anand et al. | |
| 2015/0095056 A1 | 4/2015 | Ryan et al. | |
| 2015/0095066 A1 | 4/2015 | Ryan et al. | |
| 2015/0095068 A1 | 4/2015 | Ryan et al. | |
| 2015/0112725 A1 | 4/2015 | Ryan | |
| 2015/0120328 A1 | 4/2015 | Ryan et al. | |
| 2020/0117860 A1 | 4/2020 | Anand et al. | |

FOREIGN PATENT DOCUMENTS

| | | |
|---|---|---|
| WO | 00/14618 A2 | 3/2000 |
| WO | 00/78374 A1 | 12/2000 |

(56) References Cited

FOREIGN PATENT DOCUMENTS

| WO | 01/91025 A1 | 11/2001 | |
|---|---|---|---|
| WO | WO-0191025 A1 * | 11/2001 | ............. G06F 21/64 |
| WO | 02/099600 A2 | 12/2002 | |

OTHER PUBLICATIONS

Akoglu et al., "OddBall: Spotting Anomalies in Weighted Graphs", Carnegie Mellon University, School of Computer Science, 2010, pp. 1-12.
Berkus, Josh, ""Unstructured Data" as an Oxymoron", Toolbox for IT, Available online at: <http ://it.toolbox.com/blogs/database-soup/unstructured-data-as-an-oxymoron-5588>, Sep. 1, 2005, 7 pages.
"Bioterrorism in the United States: Threat, Preparedness and Response", Chemical and Biological Arms Control Institute, Contract No. 200*1999*00132, Nov. 2000, 339 pages.
Boxwala et al., "Architecture for a Multipurpose Guideline Execution Engine", Proceedings of AIMA Symposium, 1999, pp. 701-705.
Chen et al., "Do "America's Best Hospitals" Perform Better for Acute Myocardial Infarction?", The New England Journal of Medicine, vol. 340, No. 4, Jan. 28, 1999, pp. 286-292.
Christian et al., "Evaluation of Alternative Standardized Terminologies for Medical Conditions Within a Network of Observational Healthcare Databases", Journal of Biomedical Informatics, vol. 45, Issue 4, Available online at: <https://www.sciencedirect.com/science/article/pii/S153204641200069X>, Aug. 2012, pp. 689-696.
Cook et al., "The Importance Of Medication Adherence: From The Doctor-Patient Interaction To Impact On Health Outcomes", The Forum 10, Oct. 13-15, 2010, 39 pages.
Cugola et al., "Exploiting An Event-Based Infrastructure To Develop Complex Distributed Systems", Software Engineering, Proceedings Of The 1998 International Conference On Kyoto, Japan, Apr. 19-25, 1998, pp. 261-270.
"Diabetes Health Management Award Honors Mayo Clinic's Zimmerman", PR Newswire, Available online at: <http://www.thefreelibrary.com/_/print/PrintArticle.aspx?id=65465402, Sep. 25, 2000, 3 pages.
Duda et al., "Pattern Classification—Chapter 1", Second Edition, John Wiley & Sons, 2001, pp. 14-17.
Evans et al., "Using Data Mining to Characterize DNA Mutations by Patient Clinical Features", Proc AMIA Annual Symposium Proceedings, 1997, pp. 253-257.
Fidahussein et al., "A Corpus-based Approach for Automated LOINC Mapping", Journal of the American Medical Informatics Association, 2013, pp. 1-9.
Grimes, Seth, "Structure, Models and Meaning", Intelligent Enterprise, Available online at: <http://intelligent-enterprise.informationweek.com/showArticle.jhtml?articleID=59301538>, Mar. 2005, pp. 1-2.
"Guidance for Institutional Review Boards and Clinical Investigators 1998 Update", U.S. Food and Drug Administration, Available online at: <http://www.fda.gov/ScienceResearch/SpecialTopics/RunningClinicalTrials/GuidancesInformationSheetsandNotices/ucm 113793.htm#IRBMember>, Sep. 1998, pp. 1-12.
Hansson et al., "Probabilistic Heuristic Estimates", Annals of Mathematics and Artificial Intelligence, vol. 2, Mar. 1990, pp. 209-220.
Hendrich, Ann, "How to Try This: Predicting Patient Falls", American Journal of Nursing, vol. 107, No. 11, Nov. 2007, pp. 50-58.
Herriman et al., "Patient Non-adherence—Pervasiveness, Drivers, and Interventions", Sciences Spotlight Series, vol. 2, No. 4, Aug. 2007, pp. 1-6.
Ho et al., "Impact of Medication Therapy Discontinuation on Mortality After Myocardial Infarction", Archives of Internal Medicine, vol. 166, No. 17, Sep. 25, 2006, pp. 1842-1847.
Hofer et al., "The Unreliability of Individual Physician "Report Cards" for Assessing the Costs and Quality of Care of a Chronic Disease", JAMA, vol. 281, No. 22, Jun. 9, 1999, pp. 2098-2105.
Hu et al., "A Healthcare Utilization Analysis Framework for Hot Spotting and Contextual Anomaly Detection", Annual Symposium Proceedings/AMIA Symposium, 2012, pp. 360-369.
Hudson, Mary E., "CAATS and Compliance—Computer-Assisted Audit Techniques In Health Care", Internal Auditor, vol. 55, No. 2, Apr. 1998, pp. 25-27.
Hudson et al., "The Feasibility of Using Automated Data To Assess Guideline-Concordant Care for Schizophrenia", Journal of Medical Systems, vol. 23, No. 4, 1999, pp. 299-307.
Jacobs, Lee, "Are Your Patients Taking What You Prescribe?", Physician Work Environment, The Permanente Journal, vol. 6, No. 3, 2002, pp. 1-6.
Jencks, Stephen F., "Rehospitalizations among Patents in the Medicare Fee-for-Service Program", The New England Journal of Medicine, Apr. 2, 2009, pp. 1418-1428.
Kamp et al., "Database System Support for Multidimensional Data Analysis in Environmental Epidemiology", Proceedings of the 1997 International Database Engineering and Applications Symposium, Aug. 25-27, 1997, pp. 180-188.
Kassirer, Jerome P., "The Use and Abuse of Practice Profiles", The New England Journal of Medicine, vol. 330, No. 9, Mar. 3, 1994, pp. 634-636.
King et al., "MEDUS/A: Distributing Database Management for Medical Research", Proceedings of Computer Networks Compcon 82, Sep. 20-23, 1982, pp. 635-642.
Kleissner, Charly, "Data Mining for the Enterprise", System Sciences, Proceedings of the Thirty-First Hawaii International Conference on System Sciences, vol. 7, Jan. 1998, pp. 295-304.
Kramer, Andrew, "Uniform Patient Assessment for Post-Acute Care", Division of Health Policy and Research, University of Colorado at Denver and Health Sciences Center, Jan. 25, 2006, 141 pages.
Larsen et al., "Fast and Effective Test Mining Using Linear-Time Document Clustering", Proceedings Of The Fifth ACM SIGKDD International Conference On Knowledge Discovery And Data Mining, Aug. 1999, pp. 16-22.
Lin et al., "Auditing Consistency and Usefulness of LOINC Use Among Three Large Institutions—Using Version Spaced for Grouping LOINC Codes", Journal of Biomedical Informatics, vol. 45, No. 4, Aug. 2012, pp. 658-666.
Matsubara et al., "F-Trail: Finding Patterns in Taxi Trajectories", Advances in Knowledge Discovery and Data Mining: 17th Pacific-Asia Conference on Knowledge Discovery and Data Mining, Apr. 2013, pp. 86-98.
Mills, Barbara D., "Computer Technology of the Not-Too-Distant Future", Medical Laboratory Observer, vol. 25, No. 9, Sep. 1993, p. 78.
Mitchell, Tom M., "Machine Learning and Data Mining", Communications of the ACM, vol. 42, No. 11, Nov. 1999, pp. 31-36.
Morse, Janice M., "Preventing Patient Falls", Sage Publications, 1997, 3 pages.
Nahm et al., "A Mutually Beneficial Integration of Data Mining and Information Extraction", In Proceedings of the Seventeenth National Conference on Artificial Intelligence, Jul. 30, 2000, pp. 627-632.
Orman, Gordan K., "It Takes More than Wireless to Unbind Healthcare", Presentation at Healthcare Unbound 2007 Conference, 2007, p. 7.
"Nosocomial infection", Wikipedia, Available online at: <http://en.wikipedia.org/wiki/Nosocomial_infection>, Downloaded on Jun. 2, 2011, pp. 1-9.
Ong et al., "The Colorectal Cancer Recurrence Support (CARES) System", Artificial Intelligence in Medicine, vol. 11, Nov. 1997, pp. 175-188.
Philbin et al., "Prediction of Hospital Readmission for Heart Failure: Development of a Simple Risk Score Based on Administrative Data", Journal of the American College of Cardiology, vol. 33, No. 6, 1999, pp. 1560-1566.
Pollack, Andrew, "Rising Threat of Infections Unfazed by Antibiotics", New York Times, Feb. 26, 2010, pp. 1-4.
"Promoting Greater Efficiency in Medicare", Report to Congress, MedPac, Jun. 15, 2007, 288 pages.
Rao et al., "Data Mining for Disease Management: Adding Value to Patient Records", Electromedica, vol. 68, 2000, pp. 63-67.
Rao, Ramana, "From Unstructured Data to Actionable Intelligence", IT Pro, IEEE Computer Society, Nov.-Dec. 2003, pp. 29-35.

(56) References Cited

OTHER PUBLICATIONS

Roemer et al., "Improved Diagnostic and Prognostic Assessments Using Health Management Information Fusion", IEEE Autotestcon Proceedings, IEEE Systems Readiness Technology Conference, Aug. 20-23, 2001, pp. 365-377.

"System Analysis: Software and Hardware Design of the Automated Patient Medical Record System", Available online at: <http://www.uprforum.com/Chap13.htm>, Downloaded on Jun. 3, 2010, pp. 1-87.

Waltz, Edward L., "Information Understanding Integrating Data Fusion and Data Mining Processes", Proceedings of the 1998 IEEE International Symposium in Monterey, Circuits and Systems, May 31, 1998, pp. VI-553-VI-556.

Wey et al., "Risk Factors for Hospital-Acquired Candidemia", A Matched Case Control Study, Archives of Internal Medicine, vol. 149, No. 10, Oct. 1989, pp. 2349-2353.

Zollo et al., "Automated Mapping of Observation Codes Using Extensional Definitions", Journal of the American Medical Informatics Association, vol. 7, No. 6, Nov.-Dec. 2000, pp. 586-592.

\* cited by examiner

GAP IN CARE DETERMINATION USING A GENERIC REPOSITORY FOR HEALTHCARE

CROSS-REFERENCE TO RELATED APPLICATIONS

This application is a continuation of, and claims priority to, U.S. patent application Ser. No. 16/704,958, filed on Dec. 5, 2019, entitled "Gap in Care Determination Using a Generic Repository for Healthcare," which is a continuation of U.S. patent application Ser. No. 14/331,320, filed on Jul. 15, 2014, entitled "Gap in Care Determination Using a Generic Repository for Healthcare," which is a continuation-in-part of U.S. patent application Ser. No. 14/037,469, filed Sep. 26, 2013, and entitled "Automated Medical Cohort Determination," which claims the benefit of priority to U.S. Provisional Application Ser. No. 61/846,111, filed Jul. 15, 2013, the entireties of all of which are incorporated herein, by reference.

BACKGROUND

The present embodiments relate to automated determination of a gap in care for one or more patients.

With the advent of the Meaningful Use regulation in the United States, providers (e.g., hospitals and physicians) are incentivized to switch from paper based systems for keeping medical information to Electronic Medical Records (EMR). However, this clinical data resides in many forms, such as labs, progress notes, discharge summaries, medication records, allergy tables, or other data sources, with significant differences between different providers or EMR vendors. This variability is the source of significant inefficiencies in the way data is made available for different applications, such as quality reporting or care management. In some cases, to deal with these differences, providers spend extra money to implement point-to-point, provider specific, bridges (e.g., data extraction and transformation interfaces) between each data source and each application. In other cases, an application is not able to deal with various types of data, resulting in incomplete and potentially inaccurate data that feeds into the decision making process.

Due to the above challenges, there is an increase in both true cost of ownership and time to value for the solutions present at a hospital or physician practice. Moreover, providers with lower budgets may be deterred from purchasing various solutions to relate one type of data to another. The patients may ultimately be affected too by a lack of bridging between diverse data formats. Without sufficient information from the various data sources, a gap in care for a patient or patients may not be identified in an automated process to back-stop a medical professional.

SUMMARY

In various embodiments, systems, methods and computer readable media are provided for automated determination of a gap in care. By extracting clinical data of any format from respective different sources, a data repository normalized to a generic format is created. A human readable data representation of medical quality data is translated into a machine generic data representation used for storing the extracted clinical data. A medical domain specific language may be used to interact with the data repository for identifying cohorts and gaps in care for the respective cohorts. Any rules for finding gaps in care are converted into the medical domain specific language for determining gaps. This standardization in both the data repository and rule application may allow for a true cost and time to value solution accessible to many different medical practices.

In a first aspect, a method is provided for automated determination of a gap in care. A human readable data representation of medical quality data is translated into a machine generic data representation. An electronic medical record of a patient is queried for values of attributes of a concept in the care for that patient. The values are stored in a semantically normalized data repository of the care for that patient, the semantically normalized data repository including the attributes, the values for the attributes, and the concepts of the attributes in the machine generic data representation. A processor converts a human readable medical rule of a quality measure about the care into a machine executable language for the semantically normalized data repository. The semantically normalized data repository of the care for that patient is evaluated with the rule in the language. The evaluation includes identifying a cohort associated with the rule, the patient being a member of the cohort, and determining the gap in the care of the patient for the quality measure with the rule. Information for the gap is output.

In a second aspect, a system is provided for automated determination of a gap in care. At least one memory is configured to store clinical data for a patient in a first format. A processor is configured to translate a rule from any of first and second standards into a language for the first format, apply the rule to the clinical data, and determine the gap in the care from the application of the rule to the clinical data.

In a third aspect, a non-transitory computer readable storage medium has stored therein data representing instructions executable by a programmed processor for automated determination of a gap in care. The storage medium includes instructions for extracting clinical data from different sources and in respective different formats into a unified coding of medical entities, attributes of the entities, and values of the attributes, identifying a cohort from application of logic in a medical domain-specific language of the unified coding, and determining, by the processor, the gap in care specific to the cohort from application of the logic in the medical domain-specific language of the unified coding.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

Figure 1:
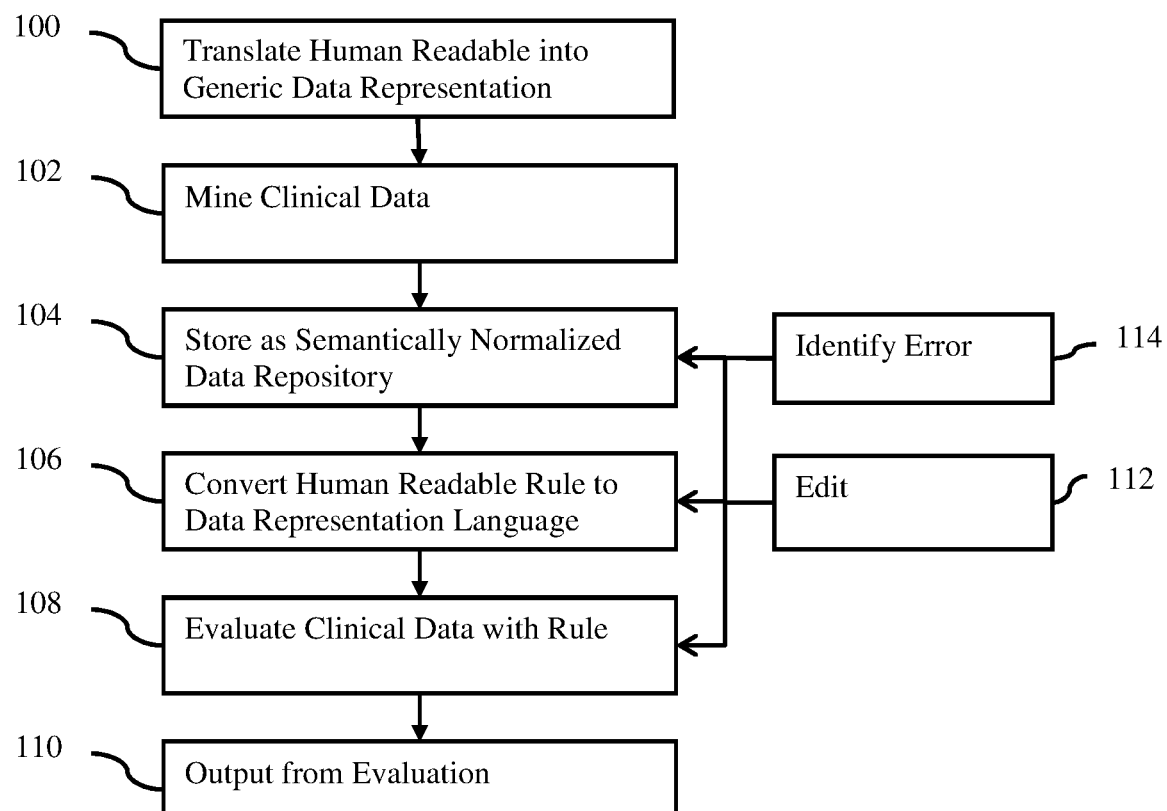
FIG. 1 is a flow chart diagram of one embodiment of a method for automated determination of a gap in care.

A framework is provided for identification of patient cohorts. For example, "patients who suffered AMI,"

"patients at risk for readmissions," or "patients likely to develop hypertension" are identified. For the people who fall in these cohorts, gaps in care may be identified. For example, AMI patients where aspirin within 24 hrs has not been administered when no contraindications are present are identified, or a diabetic patient that has not had a foot exam in the last year is identified. The gaps in care are identified automatically for the purpose of taking early actions to rectify and/or mitigate these gaps. The actions and/or interventions may be automatically recommended or implemented based on the identified gaps.

The framework creates a generic repository of clinical information from mining one or more data sources in any of various formats. Using the generic repository, rules are converted into a medical domain language that applies the rule to the clinical data as formatted for the generic repository. The rule identifies one or more cohorts for determining a gap in care of one or more members of the cohort or cohorts. An intervention may be indicated and prioritized given any determined gap. Any application may use the results from the determined gap in care.

The framework may reduce the overall true cost of ownership for the provider's information technology suite. Time to value may be reduced by having a common data model instead of various point-to-point interfaces between data repositories and various applications. The framework may allow the creation of population management solutions that are vendor and provider independent. The creation of provider independent business process modeling and/or workflows may be simplified. This modeling and workflow creation is a challenging task requiring provider specific customization without the use of the common data model. The framework may allow creation of model workflows that can become functional with minimal manual intervention. A single source of truth may be created in the normalized data repository for clinical information for all patients. The automation creates a consistent mechanism for quality reporting (e.g., for meaningful use e-measures) and monitoring adherence to care guidelines and/or best practices. Operational efficiency for care management scenarios may be increased by finding relevant cases quickly and identifying the best opportunities to make an impact based on prioritization and/or risk analysis of gaps in care and/or by triggering evidence-based care actions. The framework may increase adherence to best practices by having the ability to mitigate care gaps proactively, before it is too late to be able to make an impact. Proactive intervention may lower overall costs of healthcare by preventing at risk patients from becoming costly preventable hospital admissions.

In an exemplary embodiment, a method for automated determination of a gap in care is provided. A human readable data representation of medical quality data is translated into a machine generic data representation. A set of electronic medical data records is mined, and the results are stored into a semantically normalized data repository in the above representation. A processor translates a human readable medical rule (e.g., algorithm) representation of a quality measure into a machine executable rule format that is tied to the generic data representation. The machine executable rule is evaluated against the semantically normalized data repository. The evaluating includes identifying a cohort of patients/people associated with the rule, and determining if there is a gap in the care for the patient/person for the corresponding quality measure. Information for the gap is output.

FIG. 1 shows a method for automated determination of a gap in care. The method is implemented by or on a computer, server, workstation, system, or other device. A memory stores information. A processor, executing instructions, performs the acts, such as mining, causing storage, converting, evaluating, identifying, and outputting. Other devices may be used with or by the processor, such as a user input and display being used for editing.

The method is provided in the order shown, but other orders may be provided. For example, act 106 is performed simultaneously, in parallel, or before performing acts 102 and 104. As another example, act 112 and/or act 114 are performed after, during or before any of various of the acts 102-110.

Additional, different or fewer acts may be provided. For example, acts 110, 112, and/or 114 are not provided. As another example, acts for use of the output of act 110 are provided, such as acts for care management, workflow generation, quality reporting, and/or guideline adherence determination.

The acts are performed in response to a trigger event, such as entry of information for one or more patients into an electronic medical record. The acts are performed in real-time or during a stay at a hospital or other healthcare facility. By performing the acts during a stay, the care of the patient is tuned based on the most recent data. The care of the patient is managed based on the current status of the patient derived from patient specific data and determination of any gaps in the care. In alternative embodiments, the acts are performed as part of a batch process. Collected data is used prior to, during, or after a patient stay.

The acts are performed for a single patient. Data for that patient is used to determine one or more cohorts to which the patient belongs and any gaps in care for the cohort or cohorts. Alternatively, the acts are performed for groups of patients. The patients may be grouped by cohort, and a gap in care that occurs for multiple patients may be determined.

FIG. 1 is directed to case management at a healthcare facility. Healthcare facilities include hospitals, emergency care centers, or other locations or organizations for treating illness or injury. The patient may stay one or more days at a healthcare facility for diagnosis and/or treatment. In some cases, the stay may be only hours. Alternatively, FIG. 1 is directed to accountable care optimization, which may or may not include care at a healthcare facility. The care of the patient before, during, and after any stay at a healthcare facility is managed. For example, the care of the patient at a healthcare facility may be different (e.g., perform an extra task, such as education) in order to reduce costs for later care of the patient outside the healthcare facility or after discharge and/or in order to prevent an unplanned readmission of the patient. By identifying the gap in care, the treatment and/or diagnosis may be improved, the processes at a healthcare facility may be improved, and/or quality of care may be determined.

Figure 2:
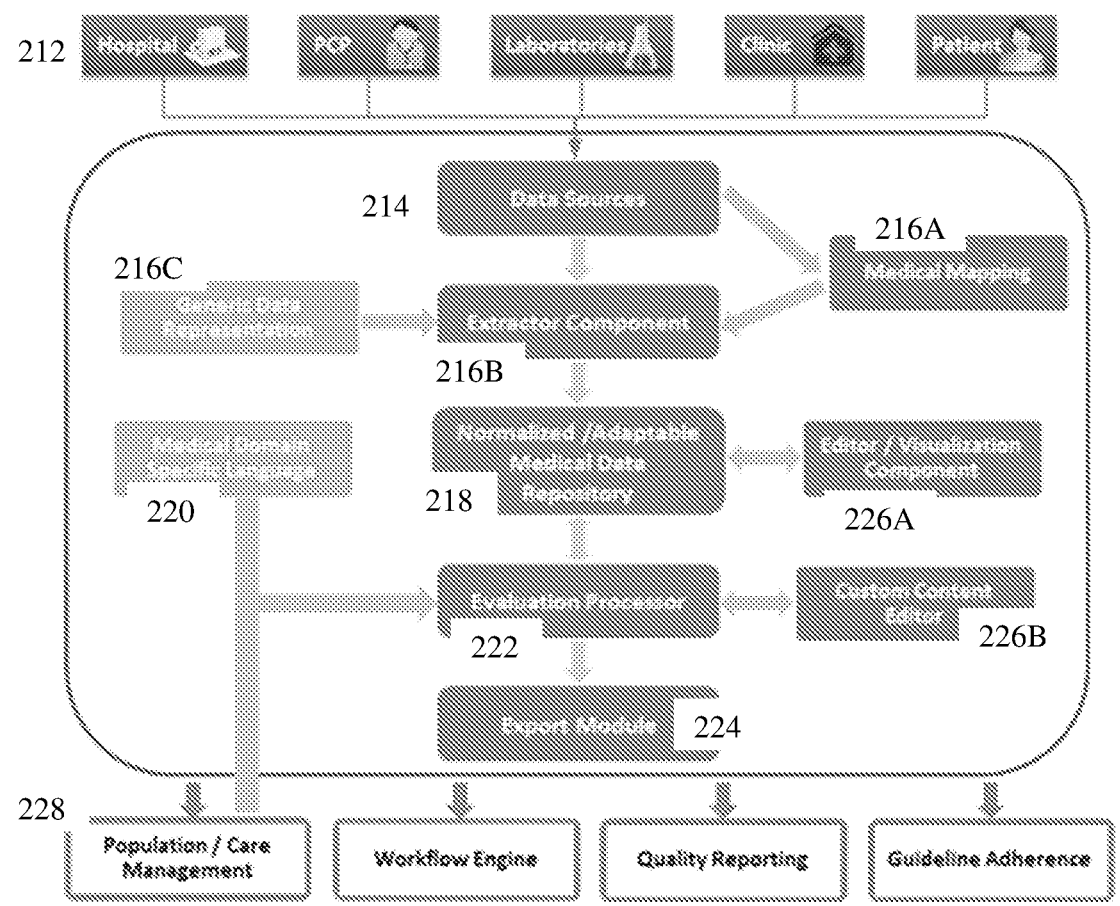
FIG. 2 is a diagram of one embodiment of an approach for automated determination of a gap in care.

FIG. 2 shows an approach for automated determination of a gap in care. The method of FIG. 1 implements the approach reflected in FIG. 2. In the detailed description below of FIG. 1, reference is also made to the conceptual representation of FIG. 2. Alternatively, FIG. 2 represents a method and/or system for determining a gap in care of one or more patients.

By mining clinical data and generating a generic or uniform format for the data despite being from many sources of data and/or applications, the data may be evaluated despite the different formats used to originally collect the data. By converting any rules for identifying cohorts and/or determining sufficiency of care into a language specific to the generic or uniform format, the clinical data may be evaluated to determine a gap in care.

Referring to FIG. 1, a human readable data representation of medical quality data is translated into a machine generic data representation. The translation is performed as needed or in a batch process.

The human readable data representation is a table, display, interface, or database representing clinical data in text and numerals that are understood by a person. For example, clinical data representing different aspects of care is labeled as variables with a descriptive name (e.g., "diagnosis") and corresponding values for the variables that are descriptive relative to the name (e.g., "cancer"). Any of the data sources may have a human readable data representation. In one embodiment, an entity, attribute, value representation of the data is used, where an entity is a concept, the attributes are characteristics or variables of the entity, and the values are values of the attributes. The human readable data representation may be from a standard, generally accepted, public, and/or government provided data model, such as the quality data model (QDM) provided by the U.S. government. QDM provides medical concepts in a standardized format.

The data in the human readable data representation is medical quality data. Medical quality data is any data related to care of a patient that may be used to determine quality of care. For example, the medical quality data is clinical data about diagnosis or treatment of the patient.

The human readable data representation is translated into a different type of data representation. Rather than human readable, coding is used that may be more efficiently used by a machine is provided. For example, the human readable data representation is semantically normalized to a well-known and standard medical terminology, such as LOINC, SNOMED, or ICD-9 in order to be accessed/queried uniformly.

The data representation is translated to a unified coding. The mining from the different data sources with many possible different formats allows storage of the data into a database with a unified coding. A given format is used for the database. Clinical data extracted from different sources and in respective different formats is stored in a unified coding. One format is used for the data mined from many different formats. In one embodiment, the unified coding is of medical entities or concepts, attributes of the entities, and values of the attributes. Alternatively, other unified coding formats for the values may be used.

The data is mined or queried to extract the concepts of interest in a generic representation. By being generic, the data may be independent of a specific implementation by a vendor or company. For example, a standardized QDM format (e.g., medical concept driven format) is used instead of the format of a specific provider of a system for storing medical records. A government body provided (e.g., Centers for Medicare and Medicaid Services), vendor agnostic, widely accepted, or standardized data description model is used. For a generic data representation reflected by the unified coding, the variables and values are stored in a manner that may be unrelated to or not tied to a specific application. For example, a radiology application stores images in a picture archiving and communications system (PACS) format. A billing system stores billing codes in another format. The information mined from the PACS format is stored in a different format. The information mined from the billing system is also stored in that different format. As another example, a medical record system from one vendor codes data in one manner (e.g., aspirin is coded as 123), and a medical record system from another vendor codes data in a different manner (e.g., aspirin is coded as xyz). These different codes are stored in the unified coding (e.g., both map to code #%*).

The Generic Data Representation (GDR) of clinical information supports longitudinal, single encounter and lifetime information about patients, their family, and their relationships. The concepts in this representation are generic (e.g. medications, allergies, problems, lab results, etc.), and are augmented with identifiers to establish the patient and where in the continuum of care (e.g. the visit) a certain piece of information belongs to. Attributes of these concepts and the corresponding values appropriate for the patient are stored in the generic data representation.

The values are stored in a semantically normalized data repository. The mined or queried data is semantically normalized by being stored in the unified coding. Different codes from different applications or data sets are converted to a same coding. One data model and/or medical ontology is used rather than supporting different data models of the different data sources. This GDR is agnostic to and can represent information from various models, such as the Quality Data Model (QDM) provided as part of the Meaningful Use Stage 2 regulation, and from various medical ontologies (e.g. UMLS, SNOMED, LOINC, etc.). The storage provides a comprehensive solution that is EMR vendor agnostic in the sense that multiple interfaces need not to be developed for use of the data. For example, electronic health records stage 1 may use the same method to access data and make safe assumptions about the data. Typically, when building applications that use data coming from other applications (e.g. a care management application using data from an electronic health records application), interfaces are developed to absorb this data. These interfaces are specific to the source (EHR) vendor. With the normalized medical data repository using the generic data representation, the data is already in a generic, vendor independent format, so the consuming application does not need to implement any interface and can consume data directly.

In act 102, an electronic medical record of one or more patients is queried. The query may be by searching or may include mining In further examples below, mining is used. The electronic medical record for the patient is a single database or a collection of databases. At represented at 212 of FIG. 2, the record may include data at or from different medical entities, such as data from a database for a hospital, data from a clinic, and/or data from a database for a primary care physician (PCP) whether affiliated or not with the hospital. Data for a patient may be mined from different hospitals. Different databases 214 at a same or different medical entities may be mined, such as mining a main patient data system, a separate radiology system (e.g., picture archiving and communication system), a separate pharmacy system, a separate laboratory system, a separate physician notes system, and/or a separate billing system. The mining may be from the patient, such as an on-line, web site, and/or application incorporating a question or questions soliciting answers from the patient. The mining from the patient may be from monitors of the patient, such as readings from a pace maker or wireless scale. Different data sources for the same and/or different medical entities are mined. Different entities may use different collection or storage applications, so the same type of data using a same type of medical record application may be in different formats.

By mining from multiple sources, a more complete representation of the patient at different times or over time is provided. Mining from multiple data sources gives a more complete picture of the patient for the continuum of care by bringing all or many of the events together. For accountable care organizations, a more complete view of the patient mined from multiple entities providing care to the patient and from multiple care providers may result in more accurate identification of gaps in the care.

The different data sources 214 have a same or different format. The mining is configured for the formats. For example, one, more, or all of the data sources are of structured data. The data is stored as fields with defined lengths, text limitations, or other characteristics. Each field is for a particular variable. The mining searches for and obtains the values from the desired fields. As another example, one, more, or all of the data sources are of unstructured data. Images, documents (e.g., free text), or other collections of information without defined fields for variables is unstructured. Physician notes may be grammatically correct, but the punctuation does not define values for specific variables. The mining may identify a value for one or more variables by searching for specific criteria in the unstructured data. In another example, the format for the data source depends on the standard, application, service provider, manufacturer, or other creator of the data source. Different formats for the same type of data may be provided, such as using different data models.

The mining is for a single patient or for a plurality of patients. The clinical data being mined is patient specific, such as locating data for one or more patients. Alternatively, the data is institution specific, such as mining data for patients of a particular medical entity (e.g., all patients of a hospital or physician).

The mining is for clinical information. Any data representation may be used. The clinical information is categorized according to a data model. For example, the values of specific variables are mined. In one embodiment, the values of attributes of a concept in the care of the patient are mined. The attributes are characteristics of the concept. The concept is a category of the care of the patient. Any resolution or level of generic and specific for the concepts may be used. For example, the concept is a medication, allergy, problem, lab result, diagnosis, or treatment. The attributes are characterizing features of the concept. For example, the concept is aspirin. The attributes are when given (time and/or date), how much (dose), and what type (brand). The values are the information populating the attributes (e.g., given=5/6/2014, and dose=100 mg). Other data representations than entity (concept), attribute, and value may be used.

The data for a patient may be reviewed for any of a list of concepts and/or attributes. Alternatively, the data for the patient is searched for values of a specific attribute and/or concept.

For mining, the values for the attributes of the concepts are extracted from multiple data sources. An Extractor Component (EC) 216B mines the data in the EMR, such as mining a records database for the patient as well as other sources (e.g., billing or claims, ambulatory, labs, radiology, clinic systems, physician practices, rehab facilities, patient self-entered Data, and/or data from one or more devices).

A processor gathers clinical data for a patient of a healthcare facility. The data is gathered by searching or by loading from the medical record. Any now known or later developed mining may be used alone or in combination.

In one embodiment, a database of the electronic medical record is mapped to a different data representation. For example, the mining is of structured information. A specific data source or field is searched for a value for a specific variable. In one embodiment, the concepts are extracted by simple mapping of existing database fields from the EMR/HL7 to the concept in another data representation. In one embodiment, mapping 216A is used to extract values to create a generic data representation 216C.

In another embodiment, parsing with natural language processing is used for mining. Free text, such as unstructured data in physician's notes, progress notes, medical imaging reports, and/or discharge summaries, is analyzed by the processor to obtain concepts, attributes, and/or values for the patient. Unstructured text is parsed by a natural language processing component of a processor. Ontologies or other sources of medical terms are used to locate the information in the free text. The sentence structure and/or semantics may be used to identify relevant information in the unstructured text. Any now known or later developed natural language processing may be used.

In another embodiment, inference reasoning is used for mining. Advanced data mining algorithms reason with uncertainty (e.g., conflicting information—nurse says patient diabetic, doctor says not diabetic) and/or reason with indirect reasoning (e.g., patient is on insulin, therefore they are diabetic). Bayes, support vector machine, or other inference-based data mining approach may be used. In one example, the values for different attributes are inferred by probabilistic combination of probabilities associated with different possible values from different sources. Each possible value identified in one or more sources are assigned a probability based on knowledge (e.g., statistically determined probabilities or professionally assigned probabilities). The possible value to use as the actual value is determined by probabilistic combination. The possible value with the highest probability is selected. The selected values are inferred values. The mining combines local and/or global evidence from medical records with the medical knowledge and guidelines to make inferences over time. Local evidence may include information available at the healthcare facilities, and global evidence may include information available from other sources, such as other healthcare facilities, insurance companies, primary care physicians, or treating physicians.

The mining occurs on an on-going basis, periodically, and/or in response to a trigger event. In one embodiment, the mining is in response to an addition or change to the electronic medical record of the patient. During a visit or at another time, an entry may be added to or altered in one of the data sources. The entry triggers the mining. For example, a new data entry is provided in the electronic medical record of the patient.

Other events may be specific points of treatment of the patient. For example, an indication of admission of a patient to a healthcare facility or new data for the patient being available is received. The receipt is by a computer or processor. For example, a nurse or administrator enters data for the medical record of a patient. The data entry indicates admission to the healthcare facility, to a practice group within the healthcare facility or to a different practice. Similarly, indication of transfer or discharge to another practice group, facility, or practice may be received. In another example, an assistant enters data showing a key trigger event (e.g., completion of surgery, assignment of the patient to another care group, completion in a task of the workflow for care of the patient, or a change in patient status).

In alternative embodiments, the indication is not received and periodic or continuous operation is provided. While data may be mined as a batch process, the data may be more actionable if mined in near real-time so gaps in care may be mitigated during a patient visit. By triggering during diagnosis or treatment, more serious patient health or financial outcomes (e.g. readmissions, complications, and/or expiration) may be avoided. In one embodiment, data is mined or processed from various sources as events are created by the source systems.

For example, in order to make sure an acute myocardial infarction (AMI) patient received a blood clot buster within 90 minutes of a heart attack, data is mined by the system as close to real-time if possible. If the mining occurs with minutes or an hour of diagnosis, gaps in care (e.g., prescription of aspirin) may be timely identified. As any new data is entered, the mining is recomputed as this new data is received. Systems that rely on batch jobs with daily or weekly periodic triggers for acquiring data and computing gaps based on this data may not be well suited for these types of scenarios.

In act 104 of FIG. 1, the mined values are stored in a semantically normalized data repository of the care for that patient or for patients. The mined information is stored in a database. The database reflects or instantiates a generic data representation of the patient.

In one embodiment, the semantically normalized data repository includes the attributes, the values for the attributes, the concepts of the attributes, associations or links between related concepts, and association or link with the patient. The values are stored with the attributes relevant for each of the concepts. The concepts are in turn linked with the identity of the patient and timing. For example, a table of concepts includes links to tables for attributes for each of the concepts. The values are stored in the tables of attributes. Other data structures may be used.

The storage creates a normalized and/or adaptable medical data repository (NMDR) 218. The extractor 216B stores the concepts for a given patient in a generic format. One example is a table for the concepts which links to a table for the attributes of the concept. A concept may be represented as a row: (e.g., ConceptId="103212", Description="Aspirin", StartDate="10/1/2010", EndDate="10/5/2010"). Corresponding attributes from a linked table or related rows are provided (e.g., Name="Dose", Value="100 mg"), (Name="MRN", Value="123"), (Name="Visit", Value="567"), (Name="Route", Value="Oral"). Other formats may be used. For example, a concept, attribute, value, timestamp format is used (e.g., column=cf: ObservationResult_SourceOrderDescription_1, timestamp=1398978338377, value=CBC With Platelet and Differential; column=cf: ObservationResult_SourceOrderName_1, timestamp=1398978338377, value=1090000; column=cf: ObservationResult_SourceResultDescription_1, timestamp=1398978338377, value=WBC; column=cf: ObservationResult_SourceResultName_1, timestamp=1398978338377, value=WBC).

The semantically normalized data repository defines the structure of the database. In one embodiment, the semantically normalized data repository allows for modification during the storing or during use of the database. For example, a relationship between concepts is added or changed, an order of attributes is changed, a new concept is added, a new attribute is added, or combinations thereof are provided during the storing. The mining may identify a concept or attribute related to a concept not included in the table or other structure of the data representation.

Sometimes it is not possible to anticipate the fields that will be part of the incoming data. To accommodate this situation, the data representation has an adaptable column architecture that allows the data columns to be created and modified during run-time as the data arrives to the system.

The columnar data storage architecture stores data in columns instead of rows as done in other databases. This makes the storage more efficient and faster. A predefined set of columns for data storage is not provided, allowing for adaptation. The columns are adaptable in the way the data is coming. The adaptable indicates that, when any new data with new columns definition is found, the column is added at run time to the database table, and, when a data is stored, only the relevant columns are stored and other columns are not stored unlike relational database where all the columns for a row have to be stored. By adding the column, the schema of the normalized medical data repository is altered. This alteration may occur at run time without reprogramming to accommodate the alteration of the schema of the database. In other embodiments, schema may not adapt, requiring a change in programming or resetting to add a column and/or row to the database.

This approach is more flexible than that of standard relational database management system where the schema is defined beforehand in great detail and each change in source data causes some amount of change to the database that will make the database unavailable for some time. In alternative embodiments, a relational database management system is used.

In act 106, a structured rule about the care is converted into a language for the semantically normalized data repository. The rule is a human readable medical rule. The rule is in text. The text is readable by a human as if in a sentence form. Alternatively, the text is readable by a human as in a program or computer language form, such as c++ or xml data.

The rule is a representation of a quality of care measure. For example, the rule reflects a guideline, standard of care, care workflow, insurance requirement, or other indication distinguishing quality or sufficient care from care outside a standard. A user may delete, edit or add any human readable medical rule. Since the rule is human readable, the user instinctively understands and can alter the rule as desired to identify the desired information from the data. A list of possible rules or a specific rule may be provided to the user or automatically used.

A processor compiles rules from any source into instructions formatted to interact with the format of the unified coding of the semantically normalized data repository. The human readable medical rule (e.g., algorithm) is translated into a machine executable rule format tied to the generic data representation. A computer language, such as a medical domain specific language (MDSL) 220, incorporates logic for interacting with the data representation, such as including calls to specific fields, reading links, and/or extracting data. The language is used to interact with the data representation.

The language is used to identify gaps in care represented by the data for the patient. The care is defined by a workflow, guideline, governing body, medical institution, insurance company, accreditation board, manually entered rule, or other source. For example, one or more guidelines are presented in a health quality measure format (HQMF) by a third party (e.g., government). This format uses xml description of the guidelines. This xml description of the guidelines is compiled into the medical domain specific language. As another example, a user enters information that defines a cohort and defines one or more events or a sequence of events that may or may not have happened for the cohort. The processor converts the events as a rule into the language for interacting with the data representation.

The rules interact with the data representation to answer higher level questions (e.g. "does a patient belong to a certain population?" or "did a patient in a population receive treatment as per best care practice guidelines?"). More specific rules may be provided, such as "did an AMI patient receive aspirin with 90 minutes of diagnosis?". Since the data representation contains semantically normalized data, the rules safely assume some characteristics about this data which allows for better mining of this data using query methods.

In act 108, a processor evaluates the semantically normalized data repository of the care for that patient with the rule in the language. For example, an evaluation processor 222 applies the rule as compiled for interaction with the unified coding to the data representation of the database.

The structured rule as compiled is a program for determining a gap in care. This MDSL program is parsed using the language. The logic resulting from the parsing is applied to the semantically normalized data repository.

The logic identifies one or more cohorts. The rule provides a cohort definition, such as identifying one or more concepts and/or attributes of concepts. A single datum or combination of data defines the cohort. For example, a "Patients with Acute Myocardial Infarction" cohort is identified based on the "Diagnosis Code" concept. A diagnosis code with an attribute for AMI having a positive value identifies the patients within the cohort. A patient is identified as being a member of the cohort. The rule converted to the language identifies the cohort, allowing identification of membership of the cohort.

The clinical data is used to determine cohort membership for a given patient. For example, based on the past and current medical records of the patient, the patient is classified into or classified as not being a member of a given cohort. Any level of cohort description may be used, such as a diagnosis-related group (e.g., AMI) as a cohort, or one of five types of myocardial infarction as a cohort.

After or as part of identifying the cohort (e.g., patients relevant for the care inquiry), a gap in care may be determined by the processor. The logic extracted from the compiled rule indicates the care that should have occurred. The rule defines the care as well as the cohort. A violation of the structured rule indicates a gap in care specific to the cohort. By applying the logic in the medical domain-specific language of the unified coding to the data of the patient, the processor determines whether a gap in care occurred. For example, the rule is that an AMI patient receives aspirin within 90 minutes. The cohort is extracted as AMI patients. The care is aspirin within 90 minutes. The logic searches the database for the aspirin concept. If the concept is not found for the patient and the value for the time attribute indicates outside of the 90 minute window, a gap in care is identified. Within the AMI patients, the ones that do not have "aspirin" found in the NMDR within a certain time frame are deemed to have a gap in their care. Any combination of concepts, attributes, and values of attributes may be used to determine a gap in care. The structured rule or rules indicate the combination of data that is expected. Alternatively, the rule indicates data that should not occur.

Any exclusions or exceptions may be applied. The rule and resulting logic in the language may include one or more exceptions or exclusions. For example, a list of contraindications is provided. If one or more of the contraindications exist in the data for the patient as a concept, attribute, or value, then the rule may not be violated and a gap in care is not determined. As another example, a list of possible allergies is provided. If the patient has an allergy related to the care (e.g., allergic to a medication), then the patient may be excluded from the cohort and no gap in care due to the allergy is identified.

In act 110, information for the gap is output. The output occurs during the visit, before a visit, or after a visit. For real-time or more rapid operation, the output is provided in order to prevent the gap in care. During the visit, the care may be provided due to the output where the care might otherwise have not occurred. The gap in care is prevented (e.g., identified in sufficient time to then satisfy the guideline or other rule). The determination of the gap in care is predictive. Alternatively, the gap in care is determined after having occurred, so the output is used for mitigation for the patient, training for medical professionals, rating of performance, or other purposes.

The information is used for care of the patient. Alternatively or additionally, an export module 224 outputs the information for other purposes (see 228), such as care management (e.g., information provided to a care manager at a hospital so that the care manager may assist in the care of the patient population), to a workflow engine (e.g., trigger an intervention, alert, mitigation, or other workflow for diagnosis or treatment of the patient), quality reporting (e.g., ranking a medical professional, hospital or other entity in satisfaction of the rule), or guideline adherence (e.g., insurance or accreditation measures about healthcare). Other uses of the information may be provided.

The information output may be output to a user, patient, system, program, processor, memory, network, or other entity. The information is data, an alert, a trigger, a workflow, or other type of information.

In one embodiment, the information is a trigger for an intervention or task, or the intervention or task itself. The intervention or task is linked to the determined gap, such as an intervention to prevent the gap (e.g., trigger workflow to prescribe medication) or an intervention to mitigate the gap (e.g., schedule an appointment or patient contact to check for problems associated with the gap in care).

In one embodiment, a processor establishes a workflow for care of the patient. The workflow of care is established in response to and/or using the information. The workflow of care itself is based on clinical guidelines, hospital treatment standards, or other sources. In other embodiments, the processor provides an alert to a medical professional to establish a workflow. In yet other embodiments, the patient and gap are added to a list for review by a case manager.

In one embodiment, an evaluation processor or process, as part of the evaluation of act 108, evaluates whether to trigger actions, tasks, and/or interventions for patients based on the care gaps identified. The decision is based on evidence-based guidelines (e.g., the structured rule) and the recommendations (e.g., standard mitigation for the gap). These guidelines and recommendations are ported to complicated rules that are listening to events for the patient in a real-time mode. Any change in the state of the patient may trigger the evaluation of the relevant rules and create the necessary interventions and/or tasks as output information to the appropriate care team member. For example, an intervention or task is changed when new data is available in the semantically normalized data repository. The change may be to update or delete the intervention of task.

The intervention and/or tasks may be to a physician, patient, family member, or other person involved in the care of the patient. Example tasks and interventions include: creating an alert to the care manager to call a patient to refill a prescription, creating a work list item for a nurse in an EMR setting to administer a certain medication to a patient in the hospital, or requesting a patient to provide information via a patient portal.

The information may be a mitigation plan or trigger a mitigation plan. The mitigation plan includes instructions, prescriptions, education materials, schedules, clinical actions, tests, visits, examinations, or other jobs that may care for the patient. The next recommended clinical actions or reminders for the next recommended clinical actions may be output so that health care personnel are better able to follow the recommendations and/or to mitigate a gap in care.

Tasks and/or interventions are scheduled based on a timeline of the workflow or mitigation plan. The tasks are scheduled automatically. The system populates the calendars or task lists of different personnel, equipment, rooms, or other resources. For example, a time for medical imaging equipment and room is reserved, and the calendar of a technician for the medical imaging system is changed to indicate an appointment for that time. Any task to be performed by someone or something is a job entry. Reservations may be scheduled in addition to or as a job entry. Tasks may be added to the workflows of different people.

In another embodiment, a job entry in a workflow of care is automatically scheduled. The computerized workflow system includes action items to be performed by different individuals. The action items are communicated to the individual in a user interface for the workflow, by email, by text message, by placement in a calendar, or by other mechanism.

The automated scheduling may be subject to approval by one or more people. The technician, physician, or nurse may be required to accept any scheduled appointment. Where an appointment is rejected, the timeline may be adjusted to a next optimal time. In another example of approval, a case manager may be required to approve of the entire timeline and/or any changes to the timeline before scheduling is attempted and/or completed.

In one embodiment, a job entry is added to the workflow of a case manager. In a retrospective analysis or in real time after identification of a problem or issue, the case manager may be tasked with avoiding the problem or issue for the same patient or other patients with a same or similar workflow of care. For example, a patient or threshold number of patients is readmitted to a hospital due to a complication. The case manager may be tasked with attempting to prevent readmission of other patients with the same workflow of care. To avoid readmission, the case manager identifies cost effective actions, such as education about post discharge treatment. The actions are added to the workflow for care as an update. The case management workflow system may monitor for issues and generate tasks or suggest changes to deal with the issues.

For the mitigation plan, the processor may generate at least one alert. The system may be configured to monitor adherence to the rule. Reminders may be automatically generated where an action item is due or past due so that health care providers or patients are better able to follow the rule.

Alerts are generated as reminders for an upcoming action. Alerts are generated for administrators, nurses or others to cause another person to act on time. Alerts are generated where an action should have occurred and data entered, but where data has not been entered. Alerts may be generated for any reason in an effort to keep to the timeline or limit further delay than has already happened.

Any type of alert may be used. The alert is sent via text, email, voice mail, voice response, or network notification. The alert indicates the task to be performed, the location, and the patient. The alert is sent to the patient, family member, treating physician, nurse, primary care physician, and/or other medical professional. The alert may be transmitted to a computer, cellular phone, tablet, bedside monitor of the patient, or other device. The alert may be communicated through a workflow system. For example, a task to be performed is highlighted when past due or due soon. The highlighting may indicate a cost for selecting between multiple past or currently due tasks. The alert may be sent to the workflow of others for analysis, such as to identify people that regularly fail to perform on time so that future costs may be saved through training or education.

The alert may include additional information. The alert may indicate a cost associated with failure to perform on time. The cohort, gap, recently acquired data, relevant data, severity, a probability associated with treatment, treatment options, or other information may be included.

The patients of the cohort and/or patients with determined gaps in care may also be risk stratified based on current and historical status. The risk stratification may inform the selection of intervention or task. Where more than one intervention is possible, the level of risk may be used to select the intervention. For example, a phone call or personal visit may be more effective at getting a patient to perform a task than an email or text message. The cost of a more personal intervention is higher. The higher cost intervention is selected where there is greater risk.

Using all these inputs the system can find the most cost effective way to engage the right care providers with patients for the purpose of optimizing the care delivered. The interventions to fix the gap in care are assigned a cost. Alternatively, a cost is learned. The cost is in time, resources, reimbursement, and/or financial. The risk may be of reoccurrence, readmission, increased financial costs, or other risk.

The risk and cost are used together to select the intervention and/or task. For example, when the severity of the patient is predicted with a greater probability from the available data, the workflow might suggest directly getting a CT instead of first getting an x-ray and then ordering a CT when the x-ray results are not sufficient to reach a conclusion. This would not only save an extra exam but would also cut on the length of stay. Another example would be to create the optimal path or the critical task map where it becomes evident which tests/procedures can be done without waiting on results from others and which should be done in order one after the other. This will make results available quickly and possibly save on some procedures and/or tests.

Rather than just rely on best or sufficient care for the gap, the best or sufficient intervention or task with optimized cost may be used. For example, different workflows for a given mitigation of a gap in care may be provided. The workflow with a lesser cost to the healthcare and/or patient facility may be selected. The selection may be based only on cost factor, such as where each workflow of care is appropriate, or based on cost factor and other variables, such as relatively weighting severity, risk, and cost factor to select between care workflow with a range of successful outcomes.

The evaluation process and resulting output has the capability to act on feedback from real-time data and data collected over time. Since the evaluation process continuously or frequently re-evaluates care gaps based on the latest data in the normalized data repository, the evaluation process has the ability to update or remove existing actions as appropriate. For example, if a notice that a diabetic patient had a foot exam is received, an alert to contact the patient for a referral for such an exam may be removed. The querying may be redone in response to addition of information to the electronic medical record of a patient. The converting may be redone in response to the human readable medical rule is updated by a source of the human readable medical rule. The source is a standards setting body, insurance company, government body, or other authority other than the medical entity treating the patient. A physician or other person involved in the treatment of the patient may alternatively or additionally change the rule and cause re-conversion. The evaluating may be redone in response to a change of the human readable medical rule or addition of data to the semantically normalized data repository. Any of the various acts may be triggered or performed again singly or in combination in response to a change or other trigger.

Yet another challenge is the effectiveness of care professionals in sifting through the ever increasing amounts of data to identify the patients where care gaps may be mitigated. For example, some care gaps are more urgent than others. As another example, some gaps are time bound, in the sense that if an intervention is missed within a time frame, then the usefulness of the intervention decreases considerably. Simply looking at the whole population and tackling all gaps in no particular order is not feasible and the more urgent items might be missed. Therefore, ability to stratify patients based on various risk measures allows care professionals to focus on gaps based on risk and available capacity. The stratification or identification of priority is output as information to the case manager.

To additionally increase the effectiveness of the care professional trying to mitigate care gaps, tasks and/or interventions may be seamlessly triggered based on evidence-based best practices. The triggering is automatic or manual. For automatic, the tasks or interventions are performed by the processor to avoid delay and/or reduce burden on the care manager. For manual, one or more options or alerts are provided. This population of the tasks for the care manager is seamless or occurs automatically, but leaves the care manager to confirm, select, and/or activate the proposed mitigation. The interventions are sorted or prioritized based on risk, cost, and/or severity. For example, an intervention like sending an alert to patient that they need to take a flu shot is less urgent/important than calling a patient regarding refilling their Beta Blocker prescription for heart failure. For selection, the possible interventions may be prioritized according to the care gap they address, but also against other interventions addressing the same care gap.

In another embodiment, the information output is an update of the semantically normalized data repository. Data is changed, added, and/or removed. The update is of a concept, attribute, and/or value in the data representation for a patient. The evaluation may output the update to the NMDR with additional processed information. For example, data can be updated for the corresponding patients in NMDR to say that the patient belongs to that cohort. Alternatively or additionally, the corresponding user interfaces (e.g., a user interface for the evaluation or for a downstream application, such as Care/Population Management) may be updated to display that data. The original data source for the data may be updated.

In another embodiment, the information output is an indication of success of an intervention. The success of tasks and/or interventions in reducing the risk and improving the health of the patient are evaluated. One or more rules may be applied to determine success. Future observed outcomes, such as identified in the data representation or received via a feedback loop from Care Management applications, are used to measure success. By searching for this indication of success in the data representation for the patient, the success of the intervention may be measured and output.

In one embodiment, the system simulates multiple workflows for a patient or group of patients and provides comparative effectiveness in terms of outcomes and also comparison of cost on the different possible outcomes. The system also provides the most optimal workflow, the workflow with best patient outcome, and/or the workflow with minimal cost for selection in future mitigations for other patients. The provider can select one of the many workflows. As more data is input into the system during the care of the patient, the workflow is updated accordingly.

In another embodiment, the information output is a performance measure. The processor determines and indicates performance information by applying one or more rules to the data representation. The performance information may be used by the case management system or a case manager to provide more effective care and/or more cost effective care. Physicians with patients that more likely comply or avoid readmissions may be utilized more than other physicians. Healthcare facilities using less costly procedures or resources with similar success or care may be used over other facilities.

The performance is calculated based on data. Any criteria may be used for measurement. The data from a cohort (e.g., past patients for a given physician, healthcare facility, or other entity) is obtained and used to determine statistics. For example, the rates of vaccination of patients by different physicians are determined. Since vaccination may avoid later costs, the cost benefit associated with this statistic or the statistic itself is used to control the management workflow. The computer attempts to schedule visits with the physicians with a greater rate of vaccination first.

In another embodiment, the information output is a report. The information, such as the data for the patient or a group of patients (e.g., cohort), is formatted into a quality reporting document architecture format. The data for the patient is exported to memory, display, or other processor by an export module. The report indicates the cohort, gap, and patient level information in a given format. The report is in a standard, EHR or provider agnostic format. One example of format is given by the QRDA-1, QRDA-2 and QRDA-3 language.

In act 112, editing is performed. While the identification of the gap and the outputs may be performed automatically by the processor without user intervention or guidance, the results, configuration, and/or approach for any of the acts may be altered manually by the user. Using a user input and display (e.g., user interface), different aspects may be edited by the user.

In one embodiment, the data sources to be mined may be edited and/or explored. For example, the extractor 216B is augmented with an editor that allows for navigating through the data available in the data sources. The user may select pieces of information or data of the data sources relevant to a concept, attribute, or value. The user may select data and/or data sources to use or not use in the mining. The user may select configuration of the mining. The user may change the data to be mined, such as resolving an ambiguity by examining the context of conflicting or non-determinative information.

In another embodiment, the semantically normalized data repository is edited. For example, a concept associated with the patient is edited. The association to the patient, an attribute, and/or a value for the concept are edited. For storing, an editor and/or visualization component 226A allows for the visualization and/or editing of the stored data or the data to be stored in the NMDR. Data may be reviewed, selected, replaced, edited, and/or changed. The data is edited for a patient or a group of patients. The data is edited prior to or after storage.

Given that some data for a patient may be on handwritten records or in electronic repositories that are isolated from the electronic medical record (e.g., $3^{rd}$ party claims processing software that cannot be mined), the extractor 216B may sometimes work with incomplete information. The editor may be used to augment and/or modify the extracted concepts (e.g., the association of the concept with the patient, attributed of the concept, and/or values of the attributes).

In one embodiment, the editor displays a list of the relevant cohorts for a patient and, within each cohort, displays the relevant concepts at a patient and/or visit level. The patient level provides data for the patient. The visit level provides data for the patient associated with a specific visit or time period. In another embodiment, the editor allows for quick navigation across a list of patients, such as allowing scrolling through the list and providing a sub-set of information for each patient in the list or as highlighted by the scrolling. The concepts are shown at a patient level grouped by cohorts to which the patient belongs. Other formats for presenting and navigating though the stored data may be used.

In yet another embodiment of the editing, the rules and/or conversion of the rules for identifying a gap in care are edited. By editing a structured rule, the limitations, exclusions, exceptions, and/or logic applied to identify a cohort and/or to determine a gap in care for a patient are altered. For rules, a custom content editor 226B allows the creation and packaging of programs written in the language for interacting with the normalized data repository. This editor allows the user to create new medical programs and/or queries that can be run against the extracted concepts. A user may use graphical programming, selections in a menu, the language itself, or other input formats to create and/or alter the questions to be applied for evaluation of the data representation. Packages of one or more rules may be distributed to users for standard or pre-determined evaluation. Any of the users may edit one or more rules of the package to create a custom evaluation of the data representation.

Other editing may be provided, such as editing the evaluation. The user may alter the results of the identification of the cohort and/or determination of a gap in care. The output information may be edited. For example, a case manager may review an established workflow for care and alter the tasks or timeline for dealing with a gap in care of a specific patient. The workflow may be examined to determine if other action is or was warranted. Future workflow action items, discharge instructions, physician education, or other actions may be performed to avoid inefficiencies or care issues in other patients using editing of the evaluation and/or output.

In act 114, an error is identified. The error is identified in the data source, the mining, the storage of the normalized data repository, the evaluation, and/or the output. For example, the error is identified in a data source before or as part of the mining. The error is identified by determining a conflict between two data sources and/or identifying a lack of data where a value, attribute, or concept is expected. A user may indicate an error as part of editing and/or review.

When an error is identified, the error is corrected and/or avoided. In the example of the error in the data source, the mining may be performed without the error (e.g., performing the mining without including a value having the error or the data source having the error). The error is avoided by not including the error or the unreliable data source. In other examples, the error is fixed manually or automatically by inference, and the operation continues using the fixed data.

Data repair and/or error forgiveness is important in the medical environment where there are many possible sources of error. Human or machine generated errors represent a common problem in the healthcare information technology systems. In one embodiment, the extractor component 216B is designed in a way so that the extractor component 216B reprocesses the data for a patient if issues and/or errors with the data received for a patient are detected. The repair process excludes the erroneous data source and reprocesses the data through the regular processing. This makes the system more robust since the system can always go back and reprocess the data in an optimized way to make fewer mistakes in the interventions created for the patients. This may improve the patient health and reduce risks for the patient.

Figure 3:
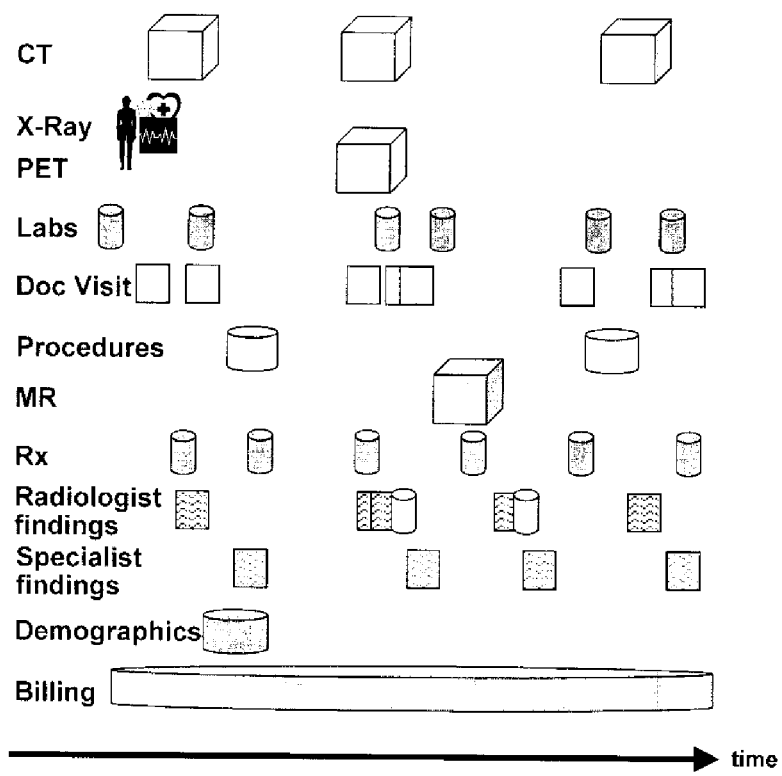
FIG. 3 shows an exemplary computerized patient record (CPR)

The generation of the semantically normalized database for the patient or patients and corresponding conversion of rules for interacting with the database allows for use of data from many sources to determine a gap in care. Healthcare providers may employ automated techniques for information storage and retrieval. As shown in FIG. 3, an exemplary electronic medical record 200 includes information collected over the course of a patient's treatment or use of an institution. This information may include, for example, computed tomography (CT) images, X-ray images, laboratory test results, doctor progress notes, details about medical procedures, prescription drug information, radiological reports, other specialist reports, demographic information, family history, patient information, and billing (financial) information.

The electronic medical record may include a plurality of data sources, each of which typically reflects a different aspect of a patient's care. Alternatively, the electronic medical record is integrated into one data source. Structured data sources, such as financial, laboratory, and pharmacy databases, generally maintain patient information in database tables of different formats. Information may also be stored in unstructured data sources, such as, for example, free text, images, and waveforms. Often, key clinical findings are only stored within unstructured physician reports, annotations on images or other unstructured data source. By mining from these various data sources and storing in a unified format, rules converted to that unified format may be applied to determine a gap in care.

Figure 4:
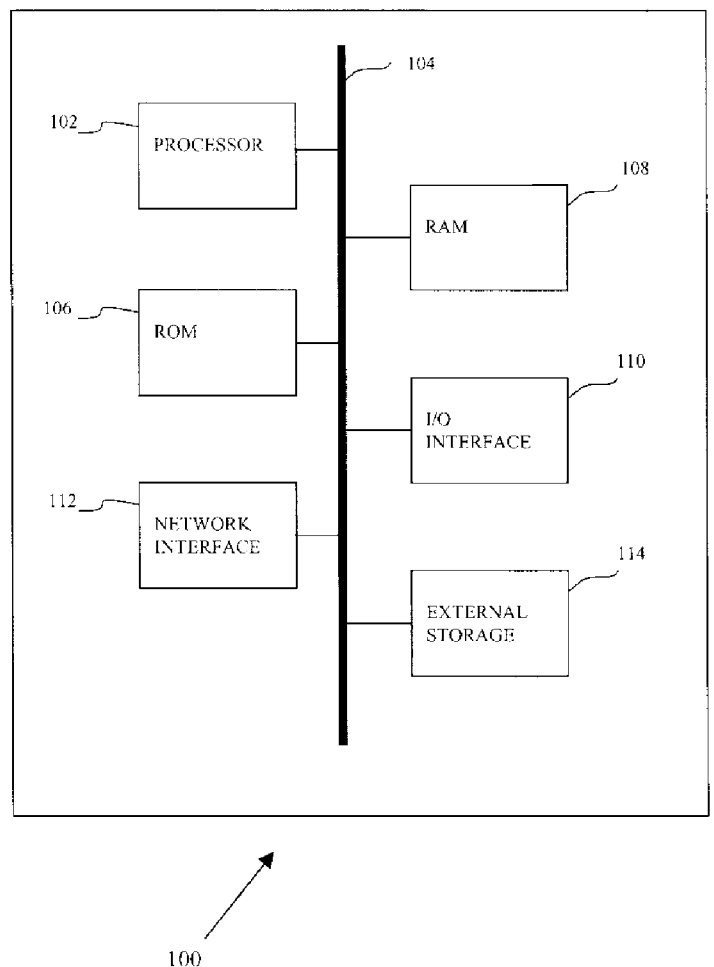
FIG. 4 shows a block diagram of a system for automated determination of a gap in care.

FIG. 4 is a block diagram of an example computer processing system 100 for implementing the embodiments described herein, such as automated determination of a gap in care. The systems, methods and/or computer readable media may be implemented in various forms of hardware, software, firmware, special purpose processors, or a combination thereof. Some embodiments are implemented in software as a program tangibly embodied on a program storage device. By implementing with a system or program, completely or semi-automated determination of a gap in care for one or more patients and output of corresponding information are provided to assist a person or medical professional.

The system 100 is a computer, personal computer, server, PACs workstation, imaging system, medical system, network processor, or other now know or later developed processing system. The system 100 includes at least one processor (hereinafter processor) 102 operatively coupled to other components via a system bus 104. The program may be uploaded to, and executed by, a processor 102 comprising any suitable architecture. Likewise, processing strategies may include multiprocessing, multitasking, parallel processing and the like. The processor 102 is implemented on a computer platform having hardware such as one or more central processing units (CPU), a random access memory (RAM), and input/output (I/O) interface(s). The computer platform also includes an operating system and microinstruction code. The various processes and functions described herein may be either part of the microinstruction code or part of the program (or combination thereof) which is executed via the operating system. Alternatively, the processor 102 is one or more processors in a network and/or on an imaging system.

The processor 102 is configured to mine data sources for data. The mining extracts data from different formats. Using mapping, inference, searching, natural language processing, and/or other extraction, data about one or more patients is mined from the different data sources. The processor 102 mines in response to a trigger, such as activation by a user, a periodic trigger, and/or a change in one of the data sources.

The mined information is formatted in a semantically normalized format. The data from different sources and different formats is altered to a given format, such as a unified coding. This generic format allows the data from different data sources to be evaluated together. Alternatively, the processor 102 is configured to use mined information, but another processor or processors perform the mining.

The processor 102 is configured to translate a rule from any of first and second standards into a language for the generic format. Rules may be expressed in various manners. For application of the rule to the normalized data, the rule is to be expressed in a manner matching the format of the normalized data. The processor 102 compiles the rule into the language for the normalized data.

Manually created rules, rules in sets, rules from third parties, or rules from other sources provide logic for identifying a cohort and determining a gap in care for the cohort. Exceptions and/or exclusions may be included in the rule. The rule may be a collection of statements, such as a program expressing multiple rules operating together. The processor 102 converts the various components of the rule into the language for the normalized data repository.

The processor 102 is configured to apply the rule to the clinical data. The rule, compiled in the language for interacting with the normalized data, is parsed. Exceptions, exclusions, and cohort identifying information are separated. Similarly, logic for indicating the care to be provided is separated. The processor 102 determines the gap in care by application of the exceptions, exclusions, and cohort identification. If the patient is a member of the cohort without an exception or exclusion, then the care of the patient represented in the data is used to determine whether the care occurred. By applying the rule to the clinical data, a gap in care is determined.

The processor 102 is configured to act upon application of the rule. The rule itself or other source may indicate action to occur for a given gap in care. In one example, statistics on a rate of gaps in care for a medical entity may be calculated. As another example, the processor 102 assigns actions to mitigate the gap or for a care manager to analyze. For example, the processor 102 initiates contact for follow-up by electronically notifying a patient in response to identifying a care plan. As another example, the processor 102 requests documentation to resolve ambiguities in a medical record. In another example, the processor 102 generates a request for clinical action likely to provide better care and/or utilization.

Clinical actions may include a test, treatment, visit, other source of obtaining clinical information, or combinations thereof. To implement case management, the processor 102 may generate a prescription form, clinical order (e.g., test order), treatment, visit, appointment, activity, or other workflow action.

In a real-time usage, the processor 102 receives currently available medical information for a patient. Based on the currently available information and mining the patient record, the processor 102 may indicate a currently appropriate class and/or establish a patient-appropriate workflow of care. The actions may then be performed during the treatment or before discharge. The processor 102 may arrange for actions to occur outside of a healthcare facility.

The processor 102 implements the operations as part of the system 100 or a plurality of systems. A read-only memory (ROM) 106, a random access memory (RAM) 108, an I/O interface 110, a network interface 112, and external storage 114 are operatively coupled to the system bus 104 with the processor 102. Various peripheral devices such as, for example, a display device, a disk storage device (e.g., a magnetic or optical disk storage device), a keyboard, printing device, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 may include any device suitable to transmit information to and from another device, such as a universal asynchronous receiver/transmitter (UART), a parallel digital interface, a software interface or any combination of known or later developed software and hardware. The network interface 112 may be linked to various types of networks, including a local area network (LAN), a wide area network (WAN), an intranet, a virtual private network (VPN), and the Internet.

One of the memories may be configured to store clinical data for one or more patients. The data is stored in the normalized format. Data from data sources is mined using the interface. The extracted clinical data is stored in a format, such as entities (e.g., concepts), attributes of the concepts, and values of the attributes in a table. One of the memories may store rules, interventions, mitigations, alerts, configuration, or other information.

The instructions and/or patient record are stored in a non-transitory computer readable memory, such as the external storage 114. The same or different computer readable media may be used for the instructions and the patient clinical data. The external storage 114 may be implemented using a database management system (DBMS) managed by the processor 102 and residing on a memory such as a hard disk, RAM, or removable media. Alternatively, the storage 114 is internal to the processor 102 (e.g. cache). The external storage 114 may be implemented on one or more additional computer systems. For example, the external storage 114 may include a data warehouse system residing on a separate computer system, a PACS system, or any other now known or later developed hospital, medical institution, medical office, testing facility, pharmacy or other medical patient record storage system. The external storage 114, an internal storage, other computer readable media, or combinations thereof store data for at least one patient record for a patient. The patient record data may be distributed among multiple storage devices or in one location.

The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method steps depicted in the accompanying figures are preferably implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

The invention claimed is:

1. A method for determination of a gap in care, the method comprising:
    mining a first data source associated with a patient for a first set of values associated with attributes of a concept in the care for the patient, the first data source being located on a first database associated with a first healthcare entity and stored in a first format;
    mining a second data source associated with the patient for a second set of values associated with attributes of the concept in the care for the patient, the second data source being located on a second database associated with a second healthcare entity and stored in a second format, wherein the first database is different than the second database, the first healthcare entity is different than the second healthcare entity, and the first format is different than the second format;
    converting the first set of values from the first format into a semantically normalized format and the second set of values from the second format into the semantically normalized format;
    storing the converted values in a semantically normalized data repository;
    evaluating the semantically normalized data repository to determine a gap in the care of the patient, wherein the gap comprises conflicting or non-determinative information in the semantically normalized data repository of the care for that patient; and
    displaying information for the gap on a user interface of a user device.

2. The method of claim 1, wherein the semantically normalized data repository is located on a third database, the third database being different than each of the first database and the second database.

3. The method of claim 1, wherein at least one of the first set of values and the second set of values is in a human readable data representation.

4. The method of claim 1, wherein the mining is in response to an addition or a change to the data source associated with the patient during a visit of the patient, and wherein outputting comprises outputting during the visit.

5. The method of claim 1, wherein at least one of the first data source and the second data source comprises an electronic medical record.

6. The method of claim 1, wherein at least one of the first data source and the second data source comprises an unstructured portion of an electronic medical record.

7. The method of claim 1, wherein the gap in the care of the patient is based on a contraindication in the first data source or the second data source.

8. The method of claim 1, wherein the gap in the care of the patient is based on an indication of a patient allergy in the first data source or the second data source.

9. The method of claim 1, wherein the method further comprises determining, based on the gap, a workflow task.

10. The method of claim 9, wherein displaying information for the gap on the user interface of the user device comprises an alert or trigger for an intervention or task.

11. The method of claim 10, wherein the method further comprises automatically scheduling the intervention or task.

12. The method of claim 11, wherein an approval request for the automatically scheduled intervention or task is displayed on the user interface of the user device.

13. The method of claim 1, wherein the gap in care of the patient comprises an indication in the first data source that the patient is diagnosed with a medical condition and an indication in the second data source that the patient does not have the medical condition.

14. The method of claim 1, wherein the gap in care of the patient comprises an indication in the first data source that the patient is receiving a medical treatment associated with a medical condition and an indication in the second data source that the patient does not have the medical condition.

15. The method of claim 1, wherein the gap in care of the patient comprises a determination that the patient is associated with an inferred medical condition based on one or more attributes of the first data source and an indication in the second data source that the patient does not have the medical condition.

16. A system for determining a gap in care, the system comprising:
    one or more computer processing configured to:
    mine a first data source associated with a patient for a first set of values associated with attributes of a concept in the care for the patient, the first data source being located on a first database associated with a first healthcare entity and stored in a first format;
    mine a second data source associated with the patient for a second set of values associated with attributes of the concept in the care for the patient, the second data source being located on a second database associated with a second healthcare entity and stored in a second format, wherein the first database is different than the second database, the first healthcare entity is different than the second healthcare entity, and the first format is different than the second format;

convert the first set of values from the first format into a semantically normalized format and the second set of values from the second format into the semantically normalized format;

cause the converted values to be stored in a semantically normalized data repository;

evaluate the semantically normalized data repository to determine a gap in the care of the patient, wherein the gap comprises conflicting or non-determinative information in the semantically normalized data repository of the care for that patient; and cause information for the gap to be displayed on a user interface of a user device.

17. The system of claim 16, wherein the gap in care of the patient comprises an indication in the first data source that the patient is diagnosed with a medical condition and an indication in the second data source that the patient does not have the medical condition.

18. The system of claim 16, wherein the gap in care of the patient comprises an indication in the first data source that the patient is receiving a medical treatment associated with a medical condition and an indication in the second data source that the patient does not have the medical condition.

19. A non-transitory computer readable media having stored therein data representing instructions executable by a programmed processor for determination of a gap in care, comprising instructions for:

mining a first data source associated with a patient for a first set of values associated with attributes of a concept in the care for the patient, the data source being located on a first database associated with a first healthcare entity and stored in a first format;

mining a second data source associated with the patient for a second set of values associated with attributes of the concept in the care for the patient, the data source being located on a second database associated with a second healthcare entity and stored in a second format, wherein the first database is different than the second database, the first healthcare entity is different than the second healthcare entity, and the first format is different than the second format;

converting the first set of values from the first format into a semantically normalized format and the second set of values from the second format into the semantically normalized format;

storing the converted values in a semantically normalized data repository;

evaluating the semantically normalized data repository to determine a gap in the care of the patient, wherein the gap comprises conflicting information in the semantically normalized data repository of the care for that patient; and displaying information for the gap on a user interface of a user device.

20. The non-transitory computer readable media of claim 19, wherein the gap in care of the patient comprises an indication in the first data source that the patient is diagnosed with a medical condition and an indication in the second data source that the patient does not have the medical condition.

* * * * *